(12) United States Patent
Kehyayan et al.

(10) Patent No.: US 6,699,204 B1
(45) Date of Patent: Mar. 2, 2004

(54) DEVICE FOR ANALYZING AUSCULTATION SOUNDS, IN PARTICULAR RESPIRATORY SOUNDS

(75) Inventors: Georges Kehyayan, 93, Avenue Henri Barbusse, F-92140 Clamart (FR); Ivan Kehayoff, 6, rue Wimpheling, F-67000 Strasbourg (FR); Gérard Lenoir, Paris (FR); Christian Avedissian, Maisons-Alfort (FR); Bruno Roux, Creteil (FR)

(73) Assignees: Georges Kehyayan, Clamart (FR); Ivan Kehayoff, Strasbourg (FR)

( * ) Notice: Subject to any disclaimer, the term of this patent is extended or adjusted under 35 U.S.C. 154(b) by 0 days.

(21) Appl. No.: 09/937,424

(22) PCT Filed: Mar. 23, 2000

(86) PCT No.: PCT/FR00/00736
§ 371 (c)(1),
(2), (4) Date: Mar. 5, 2002

(87) PCT Pub. No.: WO00/56218
PCT Pub. Date: Sep. 28, 2000

(30) Foreign Application Priority Data

Mar. 24, 1999 (FR) .......................................... 99 03682

(51) Int. Cl.[7] ................................................. A61B 5/08
(52) U.S. Cl. ...................... 600/533; 600/529; 600/586
(58) Field of Search ................................ 600/300, 529, 600/533, 586; 381/71.1, 94.1, 94.2, 94.3

(56) References Cited

U.S. PATENT DOCUMENTS

| | | | | |
|---|---|---|---|---|
| 5,058,600 A | * | 10/1991 | Schechter et al. | 600/529 |
| 5,827,195 A | * | 10/1998 | Lander | 600/509 |
| 5,928,156 A | * | 7/1999 | Krumbiegel et al. | 600/529 |
| 6,036,653 A | * | 3/2000 | Baba et al. | 600/500 |
| 6,139,505 A | * | 10/2000 | Murphy | 600/532 |
| 6,168,568 B1 | * | 1/2001 | Gavriely | 600/529 |
| 6,368,283 B1 | * | 4/2002 | Xu et al. | 600/485 |

FOREIGN PATENT DOCUMENTS

| | | |
|---|---|---|
| DE | 197 14 899 | 10/1998 |
| DE | 197 14 899 A 1 | 10/1998 |
| WO | WO 90/04945 | * 5/1990 ............ A61B/7/00 |

OTHER PUBLICATIONS

Swynghedauw et al. "Myocardial determinants in regulation of the heart rate", J Mol Med (1997) 75:860–866.*

(List continued on next page.)

Primary Examiner—Robert L. Nasser
Assistant Examiner—Patricia Mallari
(74) Attorney, Agent, or Firm—Christie, Parker & Hale, LLP (57) ABSTRACT

The invention concerns a device for analysing medical sounds, in particular respiratory sounds, comprising an input receiving a sound signal sampled in intensity levels each associated with a selected time, and storage means (2, 4, 5) comprising a processing module for evaluating, in cooperation with computing means (3), a set of transformed intensity levels, each associated with a predetermined sound frequency. It further comprises an output (26) connected to the storage means (2) for delivering each transformed intensity level in correspondence with an associated frequency, and means for representing (6, 90, 91) intensity levels transformed on the basis of frequencies, to obtain a spectral representation of the auscultation sound. The invention is characterised in that the processing module is further capable of evaluating a set of transformed intensity levels for each selected time, and the storage means (2) store each intensity level transformed on the basis of an associated frequency, and of a selected time, thereby providing a three-dimensional representation in time and in frequencies of the auscultation sound.

15 Claims, 6 Drawing Sheets

OTHER PUBLICATIONS

Oehlmann, et al. "The Reduced–Interference Local Wigner–Ville Distribution" IEEE 1997.* hhtp://www.cbi.polimi.it/glossary/WignerVille.html "Winger–Ville Distribution" Glossary of Terms Used in Time Series Analysis of Cardiovascular Data.*

V. Goncharoff, et al., "Wideband acoustic transmission of human lungs," Medical & Biological Eningeering & Computing, Sep. 1989, pp 513–519, vol. 27, No. 5, XP000046398.

* cited by examiner

FIG. 1

TIME-DOMAIN SIGNAL FIG.2A

FREQUENCY-DOMAIN SIGNAL FIG.2B

TIME-DOMAIN SIGNAL FIG.3A

FIG. 3B FREQUENCY-DOMAIN SIGNAL

FIG. 4A TIME-DOMAIN SIGNAL

FIG. 4B FREQUENCY-DOMAIN SIGNAL

FIG.5A TIME-DOMAIN SIGNAL

FIG.5B FREQUENCY-DOMAIN SIGNAL

DEVICE FOR ANALYZING AUSCULTATION SOUNDS, IN PARTICULAR RESPIRATORY SOUNDS

CROSS-REFERENCE TO RELATED APPLICATION

This application claims priority of International application number PCT/FR00/00736, filed Mar. 23, 2000, which in turn claims priority to French patent application number 99/03682, filed Mar. 24, 1999.

The present invention relates to the field of the medical analysis of acoustic noises, on the basis of mediate auscultation. It relates more particularly to a device for analyzing acoustic noises which are generated by the respiration of patients suffering from respiratory diseases such as cystic fibrosis, asthma or the like.

One of the major symptoms of cystic fibrosis consists of an infection of the respiratory tracts. Typical bronchial noises generally reveal such infections. This is because persons suffering from this disease generate accumulations of phlegm which obstruct the respiratory tracts while producing specific noises during respiration. The acoustic frequencies of the noises generated are a function of the size of these accumulations of phlegm and, in this context, the acoustic intensities associated with these frequencies may make it possible to estimate a degree of obstruction of the respiratory tracts. One danger which this disease represents is related to the rapid, progressive change in the size of the accumulations of phlegm, possibly giving rise to a progressive and irreversible limitation of the respiratory capacity of the patient.

It is appropriate then to monitor the progressive change in the abovementioned respiratory noises.

The usual practice consists of mediate auscultation, by means of a stethoscope. The frequencies heard give an indication as to the obstruction of the respiratory tracts. However, this indication is only qualitative, or even subjective. It is often difficult to describe sounds and to communicate a diagnosis on the basis of such subjective criteria.

A spectral representation of the respiratory noises, which is quantitative and reliable, is currently desirable. The interpretation of such a representation would make it possible to determine a progressive change in the disease.

Proposals for a spectral representation of the respiratory noises, these proposals being based on processing by Fourier transform, have recently come to light. However, the audio frequencies of the respiratory noises exhibit the feature of varying as a function of time, in particular as a function of the phase of respiration. Hence the information on the frequency of the noise, which changes substantially over time, is lost by Fourier-transform processing. This is because this type of processing is most suitable for signals which are stable over time.

The present invention then aims to improve the situation.

It relates to a device for analyzing mediate-auscultation noises, in particular respiratory noises, comprising:

an input for receiving a time-domain signal representative of an acoustic noise, sampled in a multiplicity of intensities each associated with a chosen instant, storage means including a processing module configured to work together with calculating means with a view to evaluating a set of transformed intensities, each associated with a predetermined audio frequency, while the storage means are further configured to store said transformed intensities in memory, and an output linked, on the one hand, to the storage means in order to deliver each transformed intensity in correspondence with an associated frequency, and, on the other hand, to means for representing the transformed intensities as a function of the frequencies, with a view to obtaining a spectral representation of the auscultation noise.

According to a general characteristic of the invention, the processing module is configured to evaluate a set of transformed intensities for each chosen instant, while the storage means are configured to store in memory each transformed intensity as a function of an associated frequency, on the one hand, and of a chosen instant, on the other hand, which makes it possible to obtain a three-dimensional representation of the auscultation noise in terms of time and of frequency.

According to a second important characteristic of the invention, the processing module is configured to evaluate the set of transformed intensities for each chosen instant, by producing, for each frequency, a sum over a multiplicity of current instants of terms resulting from a product involving, for each current instant, the intensity associated with the sum of the chosen instant and of the current instant, on the one hand, and the complex exponential of a pure imaginary product of the frequency and the current instant, on the other hand.

According to a third important characteristic of the invention, the processing module is further configured to evaluate a phase for each intensity, as a function of a difference between the associated chosen instant and a chosen start instant, with a view to attributing, to each intensity, a complex value and its conjugate value, while the terms of said sum are representative of products involving, for each current instant:

a) the complex intensity associated with the sum of the chosen instant and of the current instant, b) the conjugate complex intensity, associated with the difference in the chosen instant and in the current instant, and c) said complex exponential which makes it possible to obtain a spectral representation of the auscultation noise, while preserving a real-time scale.

According to one advantageous characteristic of the invention, the storage means further comprise chosen coefficients, for weighting of the terms of said sum, each associated with a current instant.

Advantageously, the The device as claimed in the invention includes visual-display means of the type comprising a monitor and/or a printer, while the representation means includes a graphics-representation module, able to work together with the visual-display means in order to represent the transformed intensities graphically, as a function of the associated frequencies, on the one hand, and of the chosen instants, on the other hand, forming three-dimensional spectra in terms of time and of frequencies.

Other advantages and characteristics of the present invention will emerge on examining the detailed description below and the attached drawings, in which:

The drawings, in essence, contain elements of a certain nature. They may not only serve to give a better understanding of the present invention, but also contribute to its definition, as the case may be.

Figure 1:
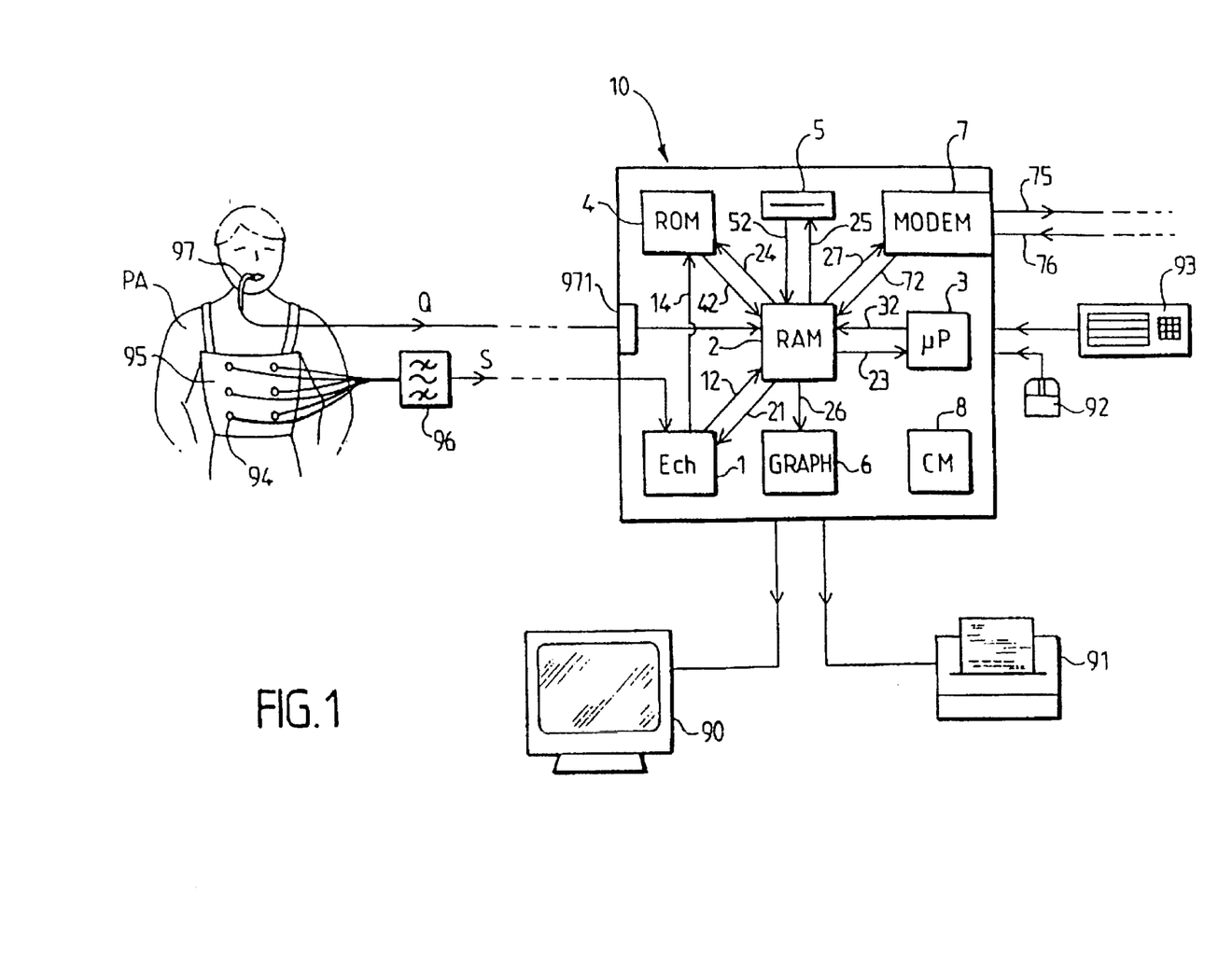
FIG. 1 diagrammatically represents a The device as claimed in the invention for analyzing noises originating from mediate auscultation.

FIG. 1 will be referred to first of all in order, by way of example, to describe a device for analyzing respiratory noises according to the invention. Overall, this device includes a processing unit (central unit 10), equipped with peripheral elements 90 to 97, connected to the central unit. In the example represented in FIG. 1, the analysis device includes a computer equipped with a monitor (screen 90), a printer 91, an input keyboard 93 and a device for selection on the screen (or mouse 92).

Furthermore, a harness 95 which the patient PA wears includes an electronic stethoscope equipped with a plurality of sensors 94 (six in the example described). These sensors are configured to work in a frequency band which is chosen in such a way as to avoid picking up noises originating from the beating of the heart of the patient PA, as well as noises from friction with the harness 95, or other noises. This frequency band typically extends from 100 Hz to about 2 kHz. The bandpass filter 96 symbolizes this function. It should be noted that, in a variant, the sensors 94 can work over a wider frequency band, while the link between the sensors 94 and the central unit 10, or else the central unit itself, include means for filtering over a limited frequency band, between about 100 Hz and 2 kHz. The audio sensors 94 are then configured to convert acoustic noise (respiratory noise) into a time-domain electrical signal (arrow S).

A respiratory-rate probe 97 may furthermore be provided (pneumotachograph in the example described), installed, for example, in a mask which the patient PA wears on his face. The probe 97 is then able to identify an instant of start of respiration, for example between inhalation and exhalation by the patient PA, on the basis of a change of sign of the respiratory rate Q.

The central unit 10 includes an interface 1 equipped with a sampler Ech (present on a sound card, for example), linked to the sensors 94, with a view to sampling the time-domain signal S. In particular, according to the Shannon theorem, it is necessary to use a sampling frequency which is greater than twice the maximum frequency of the useful signal, in order to avoid aliasing phenomena. The samples of the signal S (abovementioned multiplicity of intensities) are then stored in random-access memory 2 (RAM), with a view to processing them by a processing module of the abovementioned type, recorded in the read-only memory 4 (ROM) which the central unit 10 includes.

In order to carry out the processing of the samples by calculation, the central unit 10 is equipped with a microprocessor 3 ($\mu$P). This microprocessor is advantageously capable of working at calculation-performance rates higher than or of the order of 150 MHz. The spectra arising from the processing can be recorded in a hard disk of the central unit 10 including the read-only memory 4, or else on a removable medium 5, such as a diskette, a rewritable CD-ROM, a magneto-optical disk or other medium. A communications interface 7 may furthermore be provided, equipped with a MODEM link in order to transmit the content of the random-access memory 2 (processed spectrum) to a remote station, such as a data-interpretation station (not represented). The communications interface 7 may moreover receive samples of time-domain signals S, arising from the digitizing of respiratory noises from a remote patient (not represented), or even already processed spectra, for interpretation.

The link 72 between the modem 7 and the random-access memory 2 of the central unit 10, or else the link 12 between the sound card 1 and the random-access memory 2, in this example, then form the input of the abovementioned analysis device.

The monitor 90, as well as the printer 91, which the analysis device also includes, make it possible to view the spectra arising from the abovementioned processing. The input keyboard 93 and the mouse 92 make it possible to alter the time scales and frequencies of the spectra represented, or else to refine the choice of the abovementioned weighting coefficients.

The majority of the links between the various elements of the central unit 10, as well as the links with the peripherals, are generally controlled by a motherboard 8 (CM). With a view to preserving the clarity of FIG. 1, the links between the motherboard 8 and the elements of the central unit 10 have not been represented. It should be noted, however, that the monitor 90 is linked to the central unit 10 via a graphics card 6 (link 26), in the usual way.

The sound card 1 then receives a time-domain signal S(t) and samples this signal into a multiplicity of intensities I(n) each associated with a measurement instant n. These intensities are recorded in random-access memory 2 (link 12). In parallel, the random-access memory 2, by means of an acquisition interface 971, receives information drawn from the ventilation-rate probe 97, relating to an instant $n_0$ of the start of the measurement of the respiratory noise (start of exhalation or start of inhalation). As from the chosen start instant $n_0$, the processing module allocates a phase $\Phi[I(n)]$ to each intensity (or sample I(n)). Typically, these phases are estimated as a function of the time difference $n-n_0$. The processing module thus forms a multiplicity of complex intensities $I_c(n)$ which results from the product of the intensities I(n) and the complex exponentials of the phases associated with these intensities. These complex intensities are then expressed:

$$I_c(n)=I(n)\exp\{i\Phi[I(n)]\}, \text{ with } i^2=-1$$

On the basis of a complex intensity $I_c(n)$ associated with the predetermined instant n, it becomes possible to define a conjugate value $I_c^*(n)$ of this complex intensity. The processing module of the analysis The device as claimed in one preferred embodiment of the invention evaluates transformed intensities $I_T$ by producing the sum:

$$I_T(m, f_k) = 2 \sum_n h^2(n) I_c(m+n) I_c * (m-n) \exp(-4i\pi nf) \quad \text{(formula 1)}$$

The frequencies $f_k$, indexed according to the integer k designating the frequencies, are initially recorded in read-only memory of the central unit and are transferred via the link 42 to the random-access memory so as to carry out the calculations giving the transformed intensities $I_T$.

The coefficients associated with the instants n are initially recorded in read-only memory 4 and are also transferred via the link 42 for the calculation of the transformed intensities. These weighting coefficients h(n) can be chosen as a function of the type of respiratory noise which it is desired to process, as will be seen later on.

The transformed intensities $I_T$ then depend on a predetermined instant m, as well as on a frequency $f_k$. The processing module then carries out a "time/frequency" transformation of the sampled intensities. For example, if K frequencies $f_k$ are stored in the read-only memory 4, the processing module evaluates K values of transformed intensities $I_T$ for each predetermined instant m. In parallel, if the signal S(t) is sampled over N predetermined instants, the processing module evaluates N values of transformed intensities IT for each of the frequencies $f_k$. The processing module evaluates N×K transformed intensities in all. In practice, a conversion of spectrogram type is carried out, with 255 time points (including a central point) and 255 frequency points, within time-weighting windows or "short-term observation" windows (for example Hamming windows), allowing weighting by the coefficients h(n). In a variant, different sampling rates N can be provided, and a different number of frequencies $f_k$, depending on the requirements of the application envisaged.

From the formula 1, a three-dimensional representation of the progressive change in the transformed intensities is obtained as a function, on the one hand, of the frequencies $f_k$ and, on the other hand, of the instants m. Provision can be made to represent the transformed intensities in three-dimensional topology, for example in layers of intensities with a time scale on the x-axis and a frequency scale on the y-axis. Another possible representation, pseudo-bidimensional, is shown in FIGS. 6, 7, 8 and 9. Increasing ranges of transformed intensities are represented by different types of hachure (oblique, horizontal, crossed).

If the patient PA is suffering from cystic fibrosis, the adventitious noises generated by his respiration include specific noises, such as sibilance (whistling in relatively high frequency ranges), mild crepitation (short-term crackling) and severe crepitation (crackling which is more extended over time).

Figure 7:
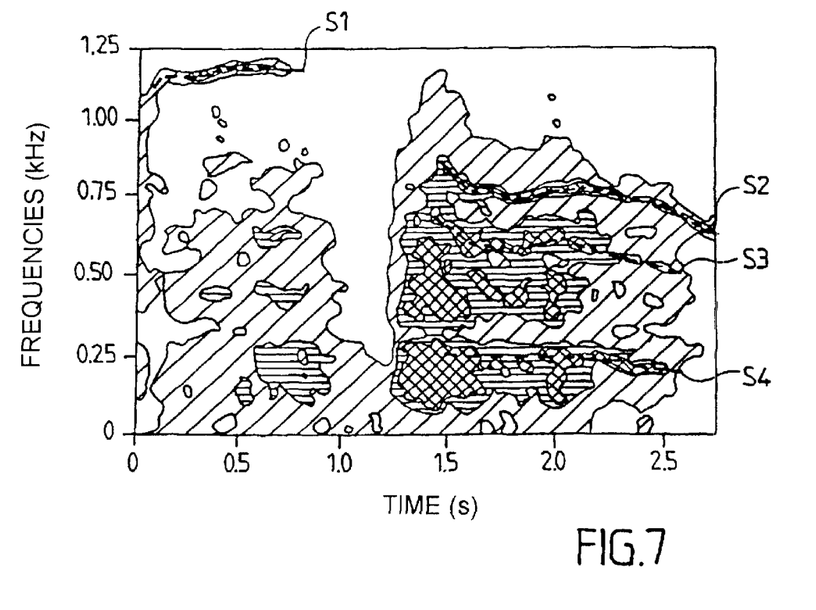
FIG. 7 is a spectral representation arising from the analysis which a The device as claimed in the invention carries out, on the basis of a time-domain signal representative of respiration noise including adventitious noise of the "sibilance" type, of the type represented in FIG. 3A.

FIG. 7 represents the progressive change, in time and in frequency, of a sibilance. A curve S2, substantially decreasing, equivalent to a "whistling" around a frequency close to 0.75 kHz, will particularly be noted as from 1.3 seconds of respiration. Such a progressive change in frequency of this whistling is difficult to detect by the usual treatment devices, which rely on fast Fourier transforms of the time-domain signal S(t) (this term being designated FFT from now on).

A fast Fourier transform of a time-domain signal S(t) is generally given by the formula:

$$I_T(f_k) = 2 \sum_n I(n) \exp(-2i\pi nf_k) \quad \text{(formula 2)}$$

Figure 2A:
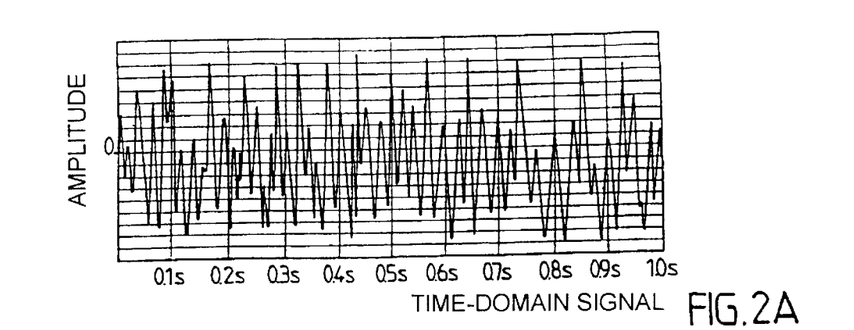
FIG. 2A represents the time-domain signal of a normal respiration noise.
Figure 2B:
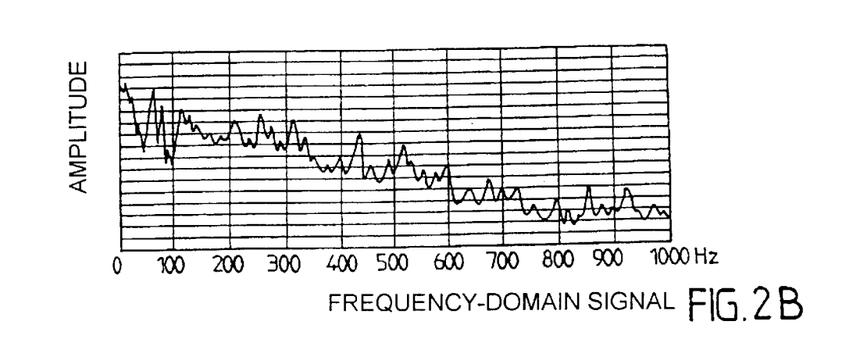
FIG. 2B is a spectral representation obtained by Fourier transform of the time-domain signal of FIG. 2A.

Referring to FIGS. 2A and 2B, the time-domain signal of normal respiratory noise (FIG. 2A) and its spectral representation (FIG. 2B), obtained by fast Fourier transforms, are represented. As long as the respiratory noise does not include components relating to a particular disease, the time-domain signal of the respiratory noise does not exhibit any periodicity and the fast Fourier transform-processing (FFT) does not include any peaks around a particular frequency.

Figure 3A:
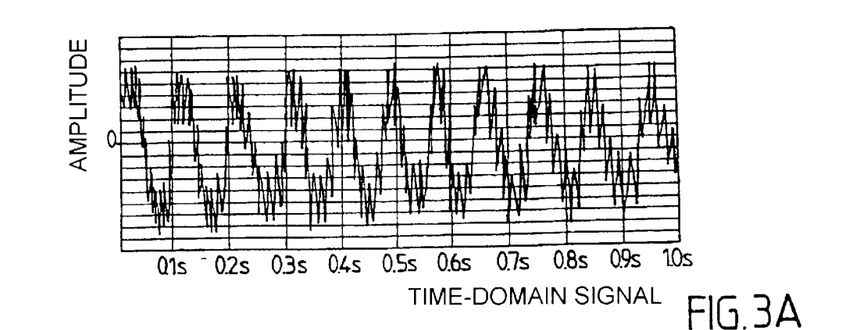
FIG. 3A represents the time-domain signal of respiration noise including adventitious noise of "sibilance" type.
Figure 3B:
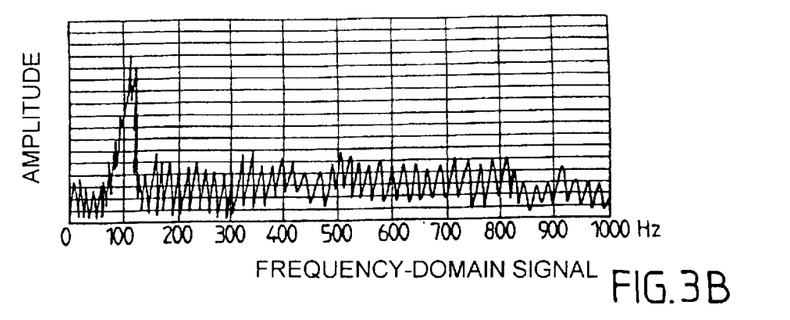
FIG. 3B is a spectral representation obtained by Fourier transform of the time-domain signal of FIG. 3A.

Referring now to FIGS. 3A and 3B, the time-domain signal of respiratory noise including a sibilance and the Fourier transform of this time-domain signal (FIG. 3) are represented. In FIG. 3B a peak will now be noticed around a frequency close to 110 Hz, indicative of this sibilance. However, if the frequency of the sibilance varies over time, FFT processing, which extends over one second of integration, will give a sibilance peak of reduced intensity and of a width extending over the entire time-domain variation of the frequency of the sibilance. Generally, such a peak is difficult to detect by conventional processing using FFTs.

Figure 4A:
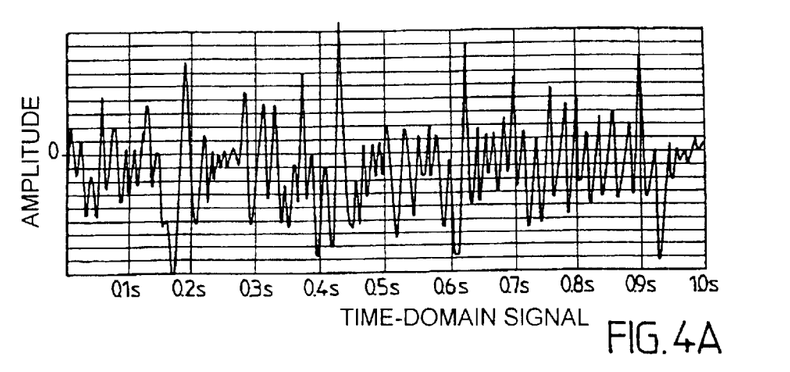
FIG. 4A represents the time-domain signal of respiratory noise including adventitious noise of the "crackling" type, in particular of "severe crepitation" type.
Figure 4B:
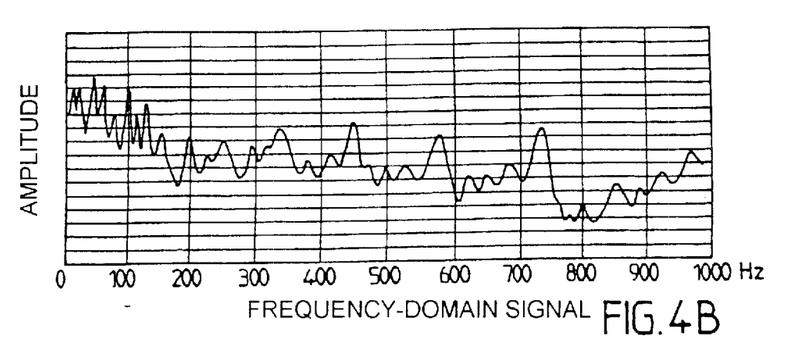
FIG. 4B is a spectral representation obtained by Fourier transform of the time-domain signal of FIG. 4A.
Figure 5A:
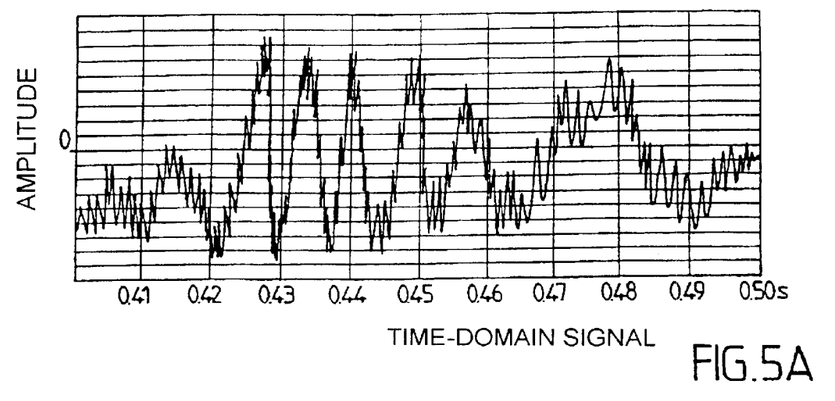
FIG. 5A represents the time-domain signal of FIG. 4A, in a reduced time scale.
Figure 5B:
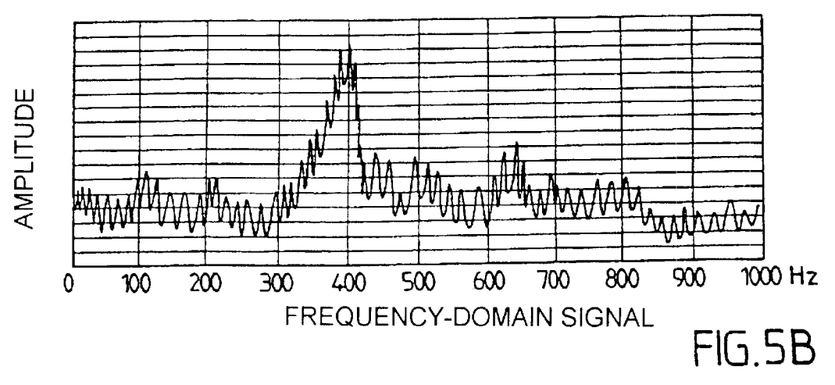
FIG. 5B is a spectral representation obtained by Fourier transform of the time-domain signal of FIG. 5A.

Referring to FIGS. 4A and 4B, a Fourier-transform analysis over a measuring interval of 1s in the example described gives only noise. In contrast, by reducing the time scale between 0.4 s and 0.5 s (FIGS. 5A and 5B) a periodicity is detected and the spectral representation obtained by FFT then exhibits a peak around 400 Hz in the example described (time-domain signal drawn from respiratory noise including severe crepitation).

Thus, in the field of the auscultatory analysis of adventitious noises (respiratory noises including crepitation, sibilance, or other noises), it is apparent that the visual processing techniques based on fast Fourier transforms are poorly adapted, in particular in the case of rapid time-domain changes in the audio frequencies or for noises to be detected which extend over short durations.

Figure 6:
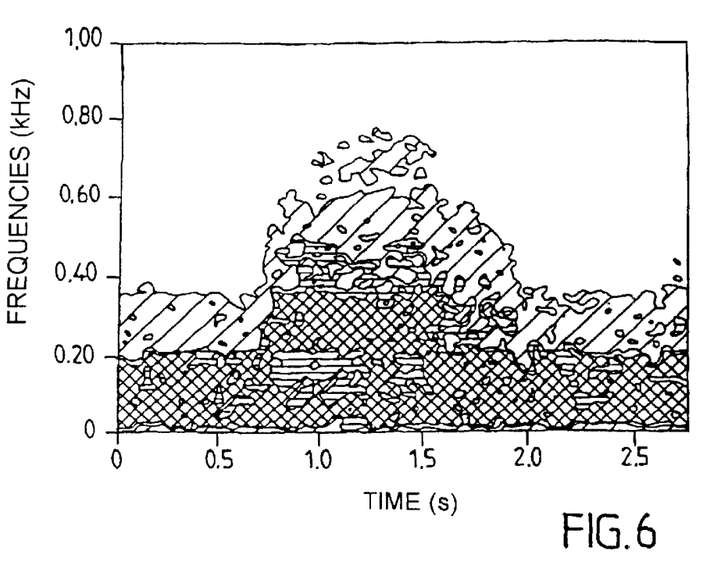
FIG. 6 is a spectral representation arising from the analysis which a The device as claimed in the invention carries out, on the basis of a time-domain signal representative of normal respiration noise, of the type represented in FIG. 2A.

FIG. 6 will now be referred to in order to describe the spectrum arising from a "time/frequency" transformation according to the invention, of a normal vesicular murmur (respiratory noise with no disease). The different types of hachure (oblique, horizontal, crossed) are representative of transformed intensity ranges (respectively increasing) as a function of a real-time scale for which the time-domain values are preserved, along the x-axis and of a frequency scale, along the y-axis. No particular spectral event is observed.

In contrast, the "time/frequency" spectrum represented in FIG. 7 brings to light substantially four sibilances which are continuous noises of a duration generally greater than or equal to 125 ms:

a first curve S1 from 0 to about 0.7 s, with a frequency stabilized around 1.15 kHz, a second curve S2 between 1.4 s and 2.7 s, of average frequency close to 0.75 kHz, a third curve S3 which extends from about 1.6 s to 2.5 s and of average frequency close to 0.55 kHz, and a fourth curve S4 between 2 s and 2.5 s, of average frequency close to 0.20 kHz.

As regards the third, substantially stable sibilance, FFT processing would have given a peak around 0.55 kHz, if this processing, however, is carried out over a time scale lying between 1.5 s and 2.5 s. In contrast, the second sibalance processed by FFT would have given a widened peak of a reduced intensity around 0.75 kHz. Furthermore, referring still to FIG. 7, it is clearly apparent that the second sibalance is the one with greatest intensity. However, FFT processing over a time scale lying between 1.5 s and 2.5 s would have favored the more time-stable sibalance (the third sibalance) and would have revealed a peak at 0.55 kHz with a higher intensity than the peak around 0.75 kHz.

This type of rale is divided into two classes depending on whether they are formed from one (monophonic) or several (polyphonic) frequencies. Thus, between 0 and 0.7 s (left-hand part of the spectrum of FIG. 7), the spectral representation of the respiratory noise reveals a monophonic sibilance, while between 1.3 s and 2.5 s, this spectral representation reveals a polyphonic sibilance (with three frequencies in the spectrum represented).

Another type of adventitious noise (or rale) concerns crackling sounds, which are discontinuous adventitious noises. The duration of these noises hardly exceeds 20 ms, in general.

Figure 8:
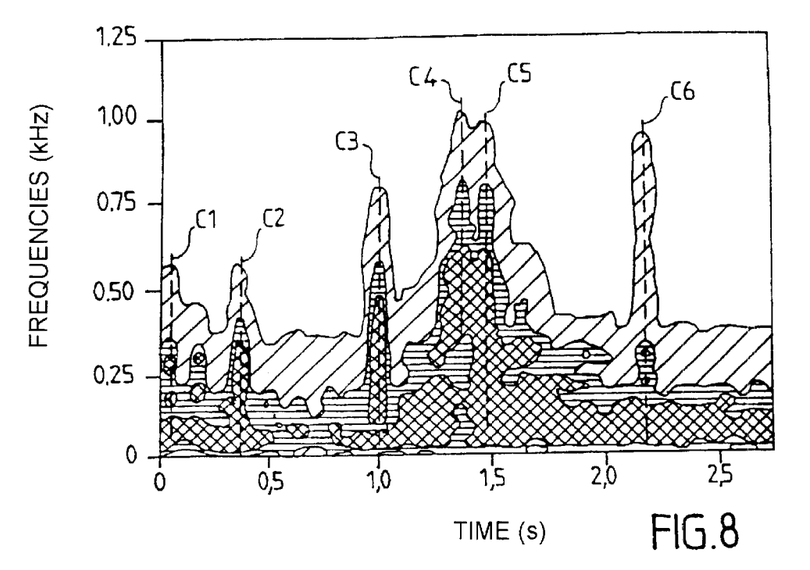
FIG. 8 is a spectral representation arising from the analysis which a The device as claimed in the invention carries out, on the basis of a time-domain signal representative of respiration noise including adventitious noise of the "slight crepitation" type.
Figure 9:
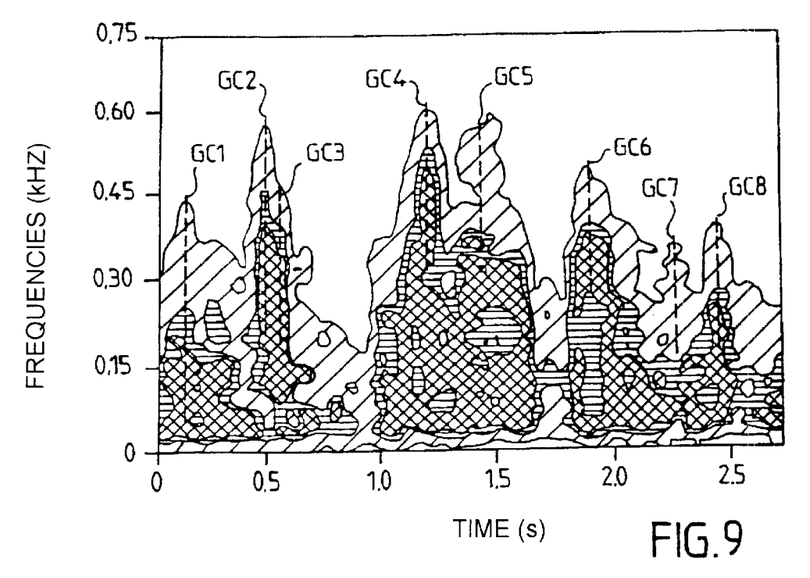
FIG. 9 is a spectral representation arising from the analysis which a The device as claimed in the invention carries out, on the basis of a time-domain signal representative of respiration noise including adventitious noise of "severe crepitation" type (time-domain signal of the type represented in FIG. 4A).

FIGS. 8 and 9 are now referred to in order to describe mild crepitation (FIG. 8) and severe crepitation (FIG. 9). In FIG. 8 pulses C1 to C6 appear, with substantially vertical tendencies, of maximum frequency close to 1 kHz. These temporally brief events correspond to mild crepitation. In FIG. 9, pulses GC1 to GC8 appear, limited in frequency to around 600 Hz and of substantially longer time duration (close to 20 ms). To the ear, these pulses correspond typically to crepitation.

In order to refine the spectral representations in time/frequency mode of the various adventitious noises from among the sibilances, mild crepitation, severe crepitation, etc., provision is made to store various sets of weighting coefficients h(n) per type of adventitious noises to be analyzed, in read-only memory of the central unit 10.

For a first analysis, a time/frequency transformation performed according to formula 1, of "pseudo Wigner-Ville" type is preferably used. However, this type of transformation generates frequency-domain and/or time-domain interference, and it is useful to carry out smoothing operations which are independent in terms of time and of frequency. Transformations of "hidden pseudo Choï-Williams" type, "Zhao-Atlas-Marks" type, or else "pseudo Born-Jordan" type make it possible to reduce the interference terms of the Wigner-Ville distribution while preserving time-domain and frequency-domain marginal distributions. Furthermore, a transformation of the "Morlet wavelet" type, corresponding to Gaussian weighting, is particularly well adapted to wideband signals including both very high and very low frequencies. Each of these transformations can be adapted to the processing of a particular type of adventitious noise.

These types of transformation, and, in particular, the mathematical principles to which they adhere, are set out especially in the following publications:

P. A. C. M. Claasen, W. F. G. Mecklen-Bräuker, Philips J. Res., vol. 35-3, p. 217–250, 1980;

H. I. Choï, W. J. Williams, IEEE Trans. On Acous. Speech On Signal Proc., vol. ASSP-37-6, p. 862–871, 1989;

Y. Zao, L. E. Atlas, R. J. Marx, IEEE Trans. On Acous. Speech On Signal Proc., vol. ASSP-38-7, p. 1084–91, 1990;

P. Goupillaud, A. Grossmann, J. Morlet, Geoexploration, vol. 33, p. 85–102, Elsevier science publishers, B. V. Amsterdam, 1984–1985.

Furthermore, for each type of transformation, a particular set of weighting coefficients h(n) can be chosen.

Moreover, in order to encourage the appearance of a particular adventitious noise, the patient PA can be asked to take up a particular body position, principally generating this adventitious noise.

Thus, after a first analysis, the content of the transformed intensities, stored in random-access memory 2, is transferred (link 26) to the graphics card 6 in the form of graphics data, which makes it possible to view a first time/frequency spectrum of the time-domain signal S(t), on the screen of the monitor 90. In order to format the graphics data for the screen, a graphics-representation module is provided, stored in the read-only memory of the central unit, with a view to graphically representing the transformed intensities as a function of the associated frequencies, on the one hand, and of the predetermined instants, on the other hand, by forming spectra of the type represented in FIGS. 6 to 9.

In order to refine the choice of the coefficients h(n), an operator, with the aid of the keyboard 93, can choose a suitable set of coefficients stored in the read-only memory of the central unit. For example, with the aid of the mouse 92, the operator may moreover select a preferred time and/or frequency scale, for viewing a detail of the spectral representation. When the desired spectral representation appears on the screen, the operator may decide to store the content of the random-access memory 2, including the transformed intensities, in read-only memory 4 of the central unit (link 24). He may moreover decide to print the spectral representation which the monitor 90 is displaying, using the printer 91. Thus, it becomes possible to compare spectra measured at different periods (for example at an interval of several days), on the basis of a spectrum stored in read-only memory 4 or printed at 91, and of a spectrum obtained recently and stored in random-access memory 2.

Provision can be made, furthermore, to follow up progressive spectral changes at different time periods, offline. In this case, several time-domain signals S(t) can be sampled and stored in read-only memory (link 14) at various periods, while the spectral analysis is carried out, off line, on a number of time-domain signals.

If it is desired, furthermore, to transfer the data relating to the transformed intensities from the central unit of a manipulator (kinesitherapeutic or other) to the unit of a doctor giving treatment (for example a specialist), the communications interface 7 (MODEM), in connection with the central unit 10, receiving the data representative of the transformed intensities (link 27 from the random-access memory 2 to the MODEM 7), sends them to the central unit of the doctor. Reciprocally, the central unit can, via the link 72 (from the MODEM to the random-access memory), receive data representative of transformed intensities or else samples of a time-domain signal S(t), measured remotely. In order to carry out this remote exchange, provision can furthermore be made to store these data on removable media 5 (links 25 and 52). Thus, the data stored on such a medium can be transferred from one analysis station to another.

Furthermore, if an operator wishes to listen to a sampled signal S(t), provision can be made to equip the sound card 1 of the central unit 10 with an earpiece connected to an output from the sound card, while the transfer of the samples from the random-access memory 2 to the sound card 1 is undertaken via the link 21 of FIG. 1.

Needless to say, the present invention is not limited to the embodiment described above by way of example. It extends to other variants.

Thus it will be understood that the choice of the transformation method (smoothed "time/frequency", Morlet wavelets or other method) is independent of the general processing of the auscultation noises which the analysis The device as claimed in the invention carries out. In fact, the choice of a type of transformation is manifested by a preferred set of weighting coefficients h(n). For example, a time/frequency transformation in which the h(n) coefficients (formula 2) are replaced by "1" (which amounts to carrying out a "double Fourier transform" in terms of time/frequency and frequency/time), would make it possible to obtain spectral representations already revealing particular adventitious noises.

Furthermore, in the context of a simplification of the processing module of the The device as claimed in the invention, provision can furthermore be made to process the sampled intensities on the basis of a simple "time/frequency" transformation involving a sum of terms representative of the product of I(m+n) and a complex exponential, in such a way that:

$$I_T(m, f_k) = \sum_n h(n) I(m+n) \exp(-2i\pi n f_k) \quad \text{(formula 3)}$$

On the basis of such a transformation, it is possible rapidly to obtain a first representation in terms of time and in frequency of the auscultation noise, which makes it possible to identify at the outset the type of adventitious noises which the patient is exhibiting.

In a general way, the present invention, needless to say, envisages the tools of the analysis device allowing it to be implemented (processing module, etc.), but also all the products resulting from its implementation (spectral representations obtained by different types of time/frequency transformations, printed on a screen or on paper, as well as all comparisons of spectra obtained by an analysis The device as claimed in the invention).

That being so, the present invention also envisages an analysis device making it possible to represent a comparison of a number of spectra, measured at different periods, in order to bring to light, for example, a deterioration or an improvement in the state of the patient. Thus the The device as claimed in the invention is equipped, furthermore, with a module for comparison of different spectra loaded into random-access memory 2, with different start instants $m_0$, with a view to detecting a progressive change in the auscultation noises by comparison of the transformed intensities and of the number of adventitious noises brought to light. Such a module is preferably stored in read-only memory 4. For example, provision can then be made for an alarm signal if, between two spectra produced at different periods, a deterioration in the state of the patient has been observed.

Thus, in one particular embodiment of the invention, the analysis device can continuously monitor the respiration of a patient, while, for example at constant time intervals, producing a "snapshot" by time/frequency transformation processing of his respiration and by comparing, for example with predetermined thresholds, the transformed intensities and/or the frequencies of the adventitious noises detected. This embodiment finds a particularly beneficial application in the monitoring of babies suffering from pulmonary infections. In such an application, provision can be made to immobilize, on the body of the baby, at least one stethoscope linked to a radio-frequency transmitter, communicating with a receiver linked, for example, to the sound card of a home computer. This computer then carries out successive spectral processing operations of the type described above and, if appropriate, without a breathing-rate probe being provided.

In the example described above, the processing module stored in read-only memory of the central unit is preferably programmed in "DSP" language, and works with a calculation manager, preferably an appropriate version of "MATHLAB" (registered trade mark). Needless to say, these choices of writing and of calculation management may allow variants, depending on progress made in the hardware available on the market. The microprocessor of the central unit may also follow these progressive changes.

In the example described above, the stethoscope which the patient carries features six sensors. Needless to say, the number of sensors of the stethoscope may be different. Furthermore, certain sensors may be arranged on the back of the patient.

Furthermore, the filtering 96 which the stethoscope carries out is described here by way of example. In another application of the analysis The device as claimed in the invention, for example for the analysis of auscultation noises from the beating of the heart of a patient, provision can be made to filter the time-domain signals received over a lower frequency band, matched to the noises from the heart. In this context, the present invention can be applied to the analysis of auscultation noises drawn from the heartbeats, or else any other auscultation noises. It may be applied, moreover, to the analysis of respiratory noises from patients suffering from asthma, or from any other respiratory disease. Thus, provision can be made furthermore for a spectral filtering (supplementary weighting coefficients $h(f_k)$ in the sum of formula 1) as a function of the type of auscultation noise which it is desired to analyze.

Furthermore, in the example described above, the analysis The device as claimed in the invention is presented in the form of a computer linked, on the one hand, to sound-pick-up means and, on the other hand, to peripherals, especially graphics representation peripherals. In a variant, the device can be presented in the form of an apparatus for specific use, for example of "DSP" (for "Digital Signal Process") type, linked to the abovementioned sound-pick-up means (stethoscopes in the example described).

Furthermore, the structure of the central unit, in the example described above, of the analysis The device as claimed in the invention is capable of variants. However, it is preferable to retain storage means (random-access memory and/or read-only memory) for the sampled intensities and for the transformed intensities, which can be addressed as a function of the sampling instants and of the sets of stored frequencies $f_k$ chosen.

What is claimed is:

1. A device for analyzing mediate-auscultation noises, in particular respiratory noises, comprising:

an input for receiving a time-domain signal (S(t)) representative of an acoustic noise, sampled in a multiplicity of intensities (I(m)) each associated with a chosen instant (m), storage means including, a processing module configured to work together with calculating means with a view to evaluating a set of transformed intensities ($I_T(f_k)$), each associated with a predetermined audio frequency ($f_k$), while the storage means are further configured to store said transformed intensities in memory, and an output (26) linked, on the one hand, to the storage means in order to deliver each transformed intensity in correspondence with an associated frequency, and, on the other hand, to means for representing the transformed intensities as a function of the frequencies, with a view to obtaining a spectral representation of the auscultation noise, characterized in that the processing module is configured to evaluate a phase for each intensity ($\Phi[I(m)]$), as a function of a difference between the associated chosen instant (m) and a chosen start instant ($m_0$), with a view to attributing, to each intensity, a complex value ($I_c(n)$) and its conjugate value ($I_c^*(n)$), in that the processing module is further configured to evaluate a set of transformed intensities ($I_T(m, f_k)$) for each chosen instant (m), by producing, for each frequency ($f_k$), a sum over a multiplicity of current instants (n) of terms resulting from a product involving, for each current instant (n),
- a) the complex intensity ($I_c(m+n)$) associated with the sum of the chosen instant (m) and of the current instant (n),
- b) the conjugate complex intensity ($I_c^*(m-n)$), associated with the difference in the chosen instant and in the current instant, and
- c) a complex exponential of a pure imaginary product of the frequency ($f_k$) and the current instant (n), and in that the storage means are configured to store in memory each transformed intensity ($I_T$) as a function of an associated frequency ($f_K$), on the one hand, and of a chosen instant (m), on the other hand, which makes it possible to obtain a three-dimensional representation in terms of time (m) and of frequencies ($f_k$) of the auscultation noise, while preserving a real-time scale.

2. The device as claimed in claim 1, characterized in that the storage means further comprise chosen coefficients (h(n)), for weighting of the terms of said sum, each associated with a current instant.

3. The device as claimed in claim 2, characterized in that the auscultation noise to be analyzed is an adventitious noise from among a set comprising sibilants, severe crepitation and mild crepitation, and in that the storage means include one set of weighting coefficients (h(n)) per type of noise to be analyzed.

4. The device as claimed in any one of the preceding claims, characterized in that it includes visual-display means of the type comprising a monitor and/or a printer while the representation means include a graphics-representation module, able to work together with the visual-display means in order to represent said transformed intensities ($I_T(m, f_k)$) graphically, as a function of the associated frequencies ($f_k$), on the one hand, and of the chosen instants (m), on the other hand, forming three-dimensional spectra in terms of time and of frequencies.

5. Device as claimed in claim 2, characterized in that it further includes input means able to work with the representation means in order to refine the time and frequency scales and/or in order to refine the choice of coefficients (h(n)) for weighting the terms of said sum.

6. Device as claimed in claim 1, characterized in that it includes a respiratory-rate probe able to define said chosen start instant ($m_0$).

7. Device as claimed in claim 1, characterized in that said storage means include a memory area for holding said transformed intensities ($I_T$), as a function of the frequencies ($f_k$) and of the associated chosen instants (m).

8. Device as claimed in claim 1, characterized in that said storage means include a memory area for holding said multiplicity of intensities ($I_T$), as a function of the associated chosen instants (m).

9. Device as claimed in claim 7 or 8, characterized in that it includes a hard disk and/or a removable medium for storing the content of said memory area.

10. Device as claimed in claim 7, characterized in that it further includes a communications interface for transmitting the content of the memory area to a remote station and/or in order to receive samples of time-domain signals (S(t)), representative of auscultation noises.

11. Device as claimed in claim 7, characterized in that it includes a comparison module, able to work together with said memory area in order to compare a number of spectral representations of auscultation noises, with different chosen start instants ($m_0$), with a view to detecting a progressive change in said auscultation noises.

12. Device as claimed in claim 1, characterized in that it includes an electronic stethoscope equipped with at least one audio sensor configured to convert acoustic noise into a time-domain electrical signal (S(t)), as well as an interface equipped with a sampler (Ech), connected to the sensor and linked furthermore to said input.

13. Device as claimed in claim 12, characterized in that the electronic stethoscope includes means for frequency filtering of the time-domain signal at the output of the sensor with a view to limiting the frequency components of the time-domain signal to a useful spectral band.

14. A method of analyzing mediate-auscultation noises respiratory of the type comprising the following stages:
- a) sampling a time-domain signal (S(t)), representative of an acoustic noise, in a multiplicity of intensities (I(m)) each associated with a chosen instant (m),
- b) evaluating a set of transformed intensities ($I_T(f_k)$), each associated with a predetermined audio frequency ($f_k$),
- c) storing said transformed intensities in memory, and
- d) delivering each transformed intensity in correspondence with an associated frequency, with a view to obtaining a spectral representation of the auscultation noise, characterized in that stage a) further includes the choice of a start instant ($m_0$), in that stage b) comprises the following operations:
- b1) evaluating a phase for each intensity ($\Phi[I(m)]$), as a function of a difference between the associated chosen instant (m) and the start instant ($m_0$), with a view to attributing, to each intensity, a complex value ($I_c(n)$) and its conjugate value ($I_c^*(n)$),
- b2) evaluating a product involving, for a current instant (n):
  - the complex intensity ($I_c(m+n)$) associated with the sum of the chosen instant (m) and of the current instant (n),
  - the conjugate complex intensity ($I_c^*(m-n)$) associated with the difference in the chosen instant and in the current instant, and
  - a complex exponential of a pure imaginary product of the frequency ($f_k$) and the current instant (n),
- b3) evaluating a set of transformed intensities ($I_T(m, f_k)$) for each chosen instant (m), by forming, for each frequency ($f_k$), a sum over a multiplicity of current instants (n) of terms resulting from the products obtained at operation b2), in that, in the course of stage c), each transformed intensity ($I_T$) is stored in memory as a function of an associated frequency ($f_k$), on the one hand, and of a chosen instant (m), on the other hand, and in that, in the course of stage d), each transformed intensity is delivered in correspondence with an associated frequency ($f_k$), on the one hand, and with a chosen instant (m), on the other hand, which makes it possible to obtain a three-dimensional representation in terms of time (m) and of frequencies ($f_k$) of the auscultation noise, while preserving a real-time scale.

15. A representation of transformed intensities in terms of time and of frequencies of a mediate-auscultation noise, which is obtained by an analysis method as claimed in claim 14.

* * * * *